United States Patent [19]

Kolattukudy et al.

[11] Patent Number: 5,545,547

[45] Date of Patent: Aug. 13, 1996

[54] ENZYMES AS AGRICULTURAL CHEMICAL ADJUVANTS

[76] Inventors: Pappachan Kolattukudy, 2301 Hoxton Ct., Columbus, Ohio 43220; Ayrookaran J. Poulose, 2540 Carmel Dr., San Bruno, Calif. 94066

[21] Appl. No.: 865,760

[22] Filed: Apr. 10, 1992

Related U.S. Application Data

[60] Continuation of Ser. No. 589,524, Sep. 28, 1990, abandoned, which is a division of Ser. No. 411,084, Sep. 22, 1989, abandoned, which is a continuation of Ser. No. 297,224, Jan. 13, 1989, abandoned, which is a continuation of Ser. No. 112,108, Oct. 19, 1987, abandoned, which is a continuation-in-part of Ser. No. 932,958, Nov. 19, 1986, abandoned.

[51] Int. Cl.$^6$ .............................. C12N 1/00; D21C 1/00; A61K 38/43; A61K 38/47
[52] U.S. Cl. .................... 435/183; 424/94.1; 424/94.61; 435/277; 435/183; 435/877
[58] Field of Search ................................ 424/94.61, 94.1; 536/20; 435/877, 277, 183

[56] References Cited

U.S. PATENT DOCUMENTS

| | | | |
|---|---|---|---|
| 3,070,497 | 12/1962 | Knight | 424/94.6 |
| 3,081,225 | 3/1963 | Farnham et al. | 424/94.6 |
| 3,493,652 | 2/1970 | Hartman | 424/94.2 |
| 3,721,733 | 3/1973 | Van Leevwen | 424/94.2 |
| 3,756,801 | 9/1973 | Herschler | 71/65 |
| 4,762,547 | 8/1988 | Iwasaki et al. | 71/65 |

FOREIGN PATENT DOCUMENTS

| | | |
|---|---|---|
| 0129315 | 12/1984 | European Pat. Off. . |
| 0197622 | 10/1986 | European Pat. Off. . |
| 0184288 | 11/1986 | European Pat. Off. ....... A01N 63/00 |

OTHER PUBLICATIONS

Fukuzumi, et al. Mokuzai Gakkai. vol. 23, No. 4, pp. 214–215 1977.
Fruton, et al., General Biochemistry, John Wiley & Sons, N.Y. pp. 574–577 (1958).
Bashkutora, et al., Mikrobiologiya 47(2): 234–40 (abstract only relied upon) (1978).
Baker, et al., Phylopathology 72(4): 420–423 (1982).
Gamborg, et al., Plant Tissue Culture, TA Thorpe Ed., Academic Press, N.Y. pp. 119–120 (1981).
Central Patent Index, Basic Abstracts Journal, Section C Week E25, 18th Aug. 1982, No. C038, 82–50855E/25, Derewent Publilcations Ltd.

*Primary Examiner*—Donald E. Czaja
*Assistant Examiner*—Jane Williams Elkin
*Attorney, Agent, or Firm*—Burns, Doane, Swecker & Mathis, L.L.P.

[57] ABSTRACT

The invention relates to a method of increasing the effect of agricultural chemicals comprising treating a plant with a plant depolymerase enzyme that will degrade plant surface polymers either prior to, or concurrently with administration of the agricultural chemical enzyme.

10 Claims, No Drawings

ENZYMES AS AGRICULTURAL CHEMICAL ADJUVANTS

CROSS REFERENCE TO RELATED APPLICATIONS

This application is a continuation of U.S. patent application Ser. No. 07/589,524 filed Sep. 28, 1990 now abandoned which in turn is a divisional application of U.S. patent application Ser. No. 07/411,084 filed Sep. 22, 1989 now abandoned which in turn is a continuation of U.S. patent application Ser. No. 07/297,224 filed Jan. 13, 1989 now abandoned which in turn is a continuation of U.S. patent application Ser. No. 07/112,108 filed Oct. 19, 1987 now abandoned which in turn is a continuation-in-part of U.S. patent application Ser. No. 06/932,958 filed Nov. 19, 1986 now abandoned.

BACKGROUND OF THE INVENTION

1. Field of the Invention

The invention relates to the use of enzymes as agricultural chemical adjuvants. Specifically, the invention relates to a method of increasing the effect of agricultural chemicals with the use of depolymerase enzymes and to compositions of depolymerase enzymes and agricultural chemical(s).

2. Background Art

Adjuvants are agents added to an agricultural chemical to increase its pharmacological effect. A wide variety of adjuvants for plant use are known representing diverse and complex chemical types and are available for use in facilitating the action of agricultural chemicals. Classified by mode of action, they include oils, surfactants (such as wetting agents, spreaders, penetrants), stabilizing agents, solvents, hygroscopic agents, deposit builders, foams and antifoam agents, buffering agents, activators, etc. These types of actions are not necessarily mutually exclusive. This great diversity of adjuvants is due largely to varying conditions that adjuvants are applied under as well as the variable results which are obtained depending on the particular agricultural chemical used. One disadvantage of many adjuvants, however, is that they are not biodegradable.

Typical agricultural chemicals include herbicides, plant growth regulators, plant species specific toxins, fungicides, insecticides, including chemical and microbial pesticides, leaf colonizing microorganisms and fertilizers. Because of the varying types of agricultural chemicals available, there is a continuing need to provide plant adjuvants with broad applicability.

SUMMARY OF THE INVENTION

It is an object of the invention to provide biodegradable agricultural chemical adjuvants and methods of increasing the pharmacological effect of agricultural chemicals using said plant adjuvants. It is also an object of this invention to provide adjuvants which allow a reduced amount of agricultural chemical to be applied to achieve a pharmacological effect.

Accordingly the invention relates to a method of increasing the pharmacological effect of agricultural chemicals comprising:

a) selecting a depolymerase enzyme which is capable of degrading at least a portion of the plant cell polymer of a plant to which an agricultural chemical is to have a pharmacological effect; and b) applying the selected agricultural to the plant either prior to or concomitantly with application of the agricultural chemical to the plant.

The invention also relates to a composition comprising a plant depolymerase enzyme and an agricultural chemical. The invention further relates to a kit of parts comprising a plant depolymerase enzyme and an agricultural chemical.

DETAILED DESCRIPTION OF THE INVENTION

In plants, the outer layers or membranes are polymeric cell structural components which are associated with waterproofing and protection. The outermost layer is normally the biopolyester cutin in the aerial parts and suberin, a polymer containing polyester domains, in the underground parts and at wound surfaces. Other membrane layers usually consists of the cell wall which contains polymers such as pectin, cellulase, hemicellulase, protein, etc. Plant cell polymers then are any polymeric layer which constitutes a major protecting barrier between the plant and its environment and also functions as a biological barrier so that diffusion of molecules can be controlled. (See Science, Vol. 208, 30 May 1980, pgs. 990–1000.)

It is an advantage of this invention in that the plant depolymerase enzyme selected for use in the invention is biodegradable. Selection of a plant depolymerase enzyme is done in accordance with the particular plant cell polymer to be degraded. So, for example, where the cell polymer is cutin, an appropriate lipase can be selected. Other depolymerase such as pectinase, hemicellulase, cellulase, and proteinase may be used alone in combination with lipase. Cutinases are preferred lipases and available from a variety of sources. See Cutinases from Fungi and Pollen, P. E. Kolattukudy, Pg. 472–504, incorporated herein by reference, for a discussion of a variety of cutinases useful in the practice of the invention. A preferred lipase is that lipase isolated from *Pseudomonas mendocina* ATCC 53552 (deposited on Oct. 15, 1986 wit the American Type Culture Collection, 12301 Parklawn Drive, Rockville, MD, 20852, U.S.A., described U.S. Ser. No. 932,959 and filled concurrently herewith, incorporated herein by reference, the lipase having the following amino acid sequence:

| 1   |     |     |     |     |     |     |     |     | 10  |     |     |
|-----|-----|-----|-----|-----|-----|-----|-----|-----|-----|-----|-----|
| ala | pro | leu | pro | asp | thr | pro | gly | ala | pro | phe | pro |
|     |     |     |     |     |     |     | 20  |     |     |     |     |
| ala | val | ala | asn | phe | asp | arg | ser | gly | pre | tyr | thr |
|     |     |     |     |     | 30  |     |     |     |     |     |     |
| thr | ser | ser | gln | ser | glu | gly | pro | ser | cys | arg | ile |

-continued

|     |     |     |     |     |     |     |     |     |     |     |
| --- | --- | --- | --- | --- | --- | --- | --- | --- | --- | --- |
|     |     |     | 40  |     |     |     |     |     |     |     |
| tyr | arg | pro | arg | asp | leu | gly | gln | gly | gly | val | arg |
|     | 50  |     |     |     |     |     |     |     |     | 60  |
| his | pro | val | ile | leu | trp | gly | asn | gly | thr | gly | ala |
|     |     |     |     |     |     |     |     |     | 70  |     |
| gly | pro | ser | thr | tyr | ala | gly | leu | leu | ser | his | trp |
|     |     |     |     |     |     | 80  |     |     |     |     |
| ala | ser | his | gly | phe | val | val | ala | ala | ala | glu | thr |
|     |     |     |     |     |     | 90  |     |     |     |     |
| ser | asn | ala | gly | thr | gly | arg | glue | met | leu | ala | cys |
|     |     |     | 100 |     |     |     |     |     |     |     |
| leu | asp | tyr | leu | val | arg | glu | asn | asp | thr | pro | tyr |
|     | 110 |     |     |     |     |     |     |     |     | 120 |
| gly | thr | tyr | ser | gly | lys | leu | asn | thr | gly | ar  | val |
|     |     |     |     |     |     |     |     |     | 130 |     |
| gly | thr | ser | gly | his | ser | gln | gly | gly | gly | gly | ser |
|     |     |     |     |     |     | 140 |     |     |     |     |
| ile | met | ala | gly | gln | asp | thr | arg | val | arg | thr | thr |
|     |     |     |     | 150 |     |     |     |     |     |     |
| ala | pro | ile | gln | pro | tyr | thr | leu | gly | leu | gly | his |
|     |     |     | 160 |     |     |     |     |     |     |     |
| asp | ser | ala | ser | gln | arg | arg | gln | gln | gly | pro | met |
|     | 170 |     |     |     |     |     |     |     |     | 180 |
| phe | leu | met | ser | gly | gly | gly | asp | thr | ile | ala | phe |
|     |     |     |     |     |     |     |     |     | 190 |     |
| pro | tyr | leu | asn | ala | gln | pro | val | tyr | arg | arg | ala |
|     |     |     |     |     |     | 200 |     |     |     |     |
| asn | val | pro | val | phe | trp | gly | glu | arg | arg | tyr | val |
|     |     |     |     | 210 |     |     |     |     |     |     |
| ser | his | phe | glu | pro | val | gly | ser | gly | gly | ala | tyr |
|     |     |     | 220 |     |     |     |     |     |     |     |
| arg | gly | pro | ser | thr | ala | trp | phe | arg | phe | gln | leu |
|     | 230 |     |     |     |     |     |     |     |     | 240 |
| met | asp | asp | gln | asp | ala | arg | ala | thr | phe | tyr | gly |
|     |     |     |     |     |     |     |     |     | 250 |     |
| ala | gln | cys | ser | leu | cys | thr | ser | leu | leu | trp |
| ser | val | gly | arg | arg | gly | leu |     |     |     |     |

However, the *Pseudomonas mendocina* strain may be cultured in a conventional medium. Liquid or solid culture may be used. Submerged aeration culture is preferable. A conventional nutrient medium can be used. Culturing temperature may vary depending on the desired rate of growth of the microorganisms and is preferably at 25°–35° C. Culturing time can be selected as desired, and is 15–50 hours. Culturing may be terminated when the highest concentration of lipase is present in the medium.

Lipase is accumulated in the fermentation broth, and extraction of the produced enzyme from the broth can be effected as follows. Cells and cell debris are first removed from the whole cell broth culture by microfiltration and centrifugation, followed by ultra-filtration to concentrate the lipase. Excess salts and color are then removed by dialysis or diafiltration.

The crude enzyme solution can then be purified. A powder of the enzyme can be obtained by lypholization and used in the various applications.

Further, one could use selective replacement of amino acids to produce lipases or other depolymerase enzymes which are more selective for the particular cutin or other polymer.

Agricultural chemicals for administration to a plant are widely varied, as discussed earlier, in both type and action. The one thing that agricultural chemicals have in common is an increase in action when systemic absorption is increased.

The enzyme selected should be in a concentration great enough to degrade at least a portion of the corresponding polymer. This amount will vary from enzyme to enzyme and from plant to plant as well as be affected by conditions such as temperature, humidity, soil, etc. One skilled in the art would be able to select such amounts without undue experimentation, but in general it is preferred that at least about one microgram per $Cm^2$ of plant surface area applied would be desirable to achieve an adjuvant effect. The enzyme may be applied either prior to or concomitantly with the desired agricultural chemical. Enzymes may be mixed with an appropriate diluant (e.g. water) to achieve ease of application, for example, by spraying. So for example, between about 1 mg. and 0.01 mg. of enzyme per ml of water may be mixed and applied at about 40 gallons/acre either with or without a desired agricultural chemical. Preferred concentrations are between 0.05 mg and 0.5 mg of depolymerase per ml of solvent. It is a further advantage of this invention that agricultural chemicals that normally need to be applied to the roots or to the soil for uptake (e.g. strazine) can now be applied to the leaf or other similar structure for effect or additional effect.

The following examples are representative only and not intended to be limiting. One skilled in the art would be able to select appropriate other depolymerase enzymes other than the lipase shown or those described herein based on the disclosures and upon reading of the representative examples given a specific plant and corresponding agricultural chemical.

DESCRIPTION OF THE PREFERRED EMBODIMENTS

EXAMPLE 1

(A) Seeding and Fermenting

A seed medium was prepared with 0.6% nutrient broth (Difco) and 1% glucose (pH 6.5). 100 ml of this medium was sterilized in 500 ml fernbach flasks. The flasks were each seeded with a loopful from an overnight culture of *P. mendocina* ATCC 53552 grown on nutrient agar, and placed on a Newbrunswick shaker at 250 rpm, 37° C. for 12 hours. The incubated 12-hour culture was then seeded at appropriate volumes (1–10% v/v) into a 1 liter fermenter (250 ml working volume), a 15 liter Biolafitte fermenter (12 liters working volume), or a 100 liter Biolafitte fermenter provided with a temperature controller, RPM, airflow and pressure controller. The fermenter medium contained 0.6% nutrient broth (Difco), 0.3% apple cutin, and 0.2% yeast extract (Difco), with an initial pH of 6.5. The medium was adjusted to pH 6.8 and sterilized for 40 minutes before seeding. Bacterial growth and enzyme production were allowed to continue in the fermenter for 12–15 hours.

(B) Enzyme Recovery by Microfiltration

The crude fermentation culture was first filtered in a Amicon unit outfitted with two Romicon microporous membranes (0.22μ) to remove cells. Remaining enzyme in the retentate which was bound to the cutin particles was removed by centrifugation. Total recovery approached 90%.

(C) Concentration and Dialysis of Whole Cell Filtrate

The recovered filtrate from the Amicon unit was concentrated to a volume of 3 liters on an Amicon ultrafiltration unit with two Romicon Pm 10 modules. The concentrated material was then dialyzed with 20 liters of 0.01M phosphate buffer, pH 7.5, to remove salts and color. Recovery at this stage averaged about 80%. Total activity for this crude preparation was $8.68 \times 10^6$ units. A unit of lipase activity is defined as the amount of enzyme which results in an increase of absorbance at 415 nm of 1.0/minute when incubated at 25° C. with 2.0 mM p-nitrophenylbutyrate in 0.1M pH 8.0 Tris-HCl buffer containing 0.1 wt. adjuvant Triton X-100.

EXAMPLE 2

Lipase Activity After Ultrafiltration and Diafiltration

The binding of three p-nitrophenyl substrates and the turnover kinetics were studied for the crude preparation of Example 1(C), where reaction conditions were 0.1M Tris with 0.1 wt. adjuvant Triton X-100, pH 8.0, at 25° C. The substrates were p-nitrophenyl caprylate, p-nitrophenyl laurate, and p-nitrophenyl palmitate, and the data is set out in Table 1.

TABLE 1

| Substrate | $K_m(\mu M)$ | $V_{max}(\mu mole/min/mg\ protein)$ |
|---|---|---|
| PNPC | 214 | 802 |
| PNPL | 167 | 214 |
| PNPP | 183 | 112 |

The Example 1(C) preparation was used in a variety of experiments; however, the Example 1(C) preparation includes two enzymes designated "Lipase 1" and "Lipase 2". Lipase 1 is the better perhydrolase. A separation and purification of the crude Example 1(C) preparation is described in Example 3, a complete separation of Lipase 1 and Lipase 2 is described in Example 4 (preferred to obtain substantially enzymatically pure Lipase 1), and an extremely pure sample of Lipase 1 preparation (i.e., analytically pure for sequencing) is described in Example 5.

EXAMPLE 3

Partial Purification of Lipase 1 and Lipase 2 by Ion Exchange and Gel Permeation Chromatography Lipase 1 was initially partially purified from the *Pseudomonas mendocina* fermentation broth by DEAE Sephacryl chromatography followed by Sephadex G-100 gel permeation chromatography. A DEAE column was equilibrated in 10 mM sodium phosphate buffer, pH 8, and the crude protein was applied to the column in the same buffer. PNB (p-nitrophenyl butyrate) lipase activity that was not bound to the column was associated with Lipase 1. Lipase 1 thus obtained from the DEAE step was subjected to chromatography on Sephadex G-100 in 10 mM sodium phosphate buffer pH 8. Lipase 1 eluted from this column as a discrete peak, and was identified by PNB hydrolase activity as well as perhydrolytic activity.

EXAMPLE 4

Complete Separation of Lipase 1 and Lipase 2 by Hydrophobic Chromatography

Lipase 1 may be separated completely from Lipase 2 by chromatography on hydrophobic resins. The enzyme solution of Example 1(C) after ultrafiltration and diafiltration was adjusted to 0.1M NaCl and applied to a 0.89×7 cm octyl Sepharose column equilibrated in 10 mM Tris(Cl) pH 8, 0.5M NaCl and washed to remove unbound protein. The following washes were then employed: 10 mM Tris(Cl), pH 8, 2M urea; 10 mM Na phosphate pH 8; 10 mM phosphate, pH 8, 0.5M NaCl. After washing, the column was then developed with a linear gradient to 50% n-propanol. The column fractions were then assayed for activity on p-nitrophenyl butyrate (PNB) and p-nitro-phenyl caprylate (PNC) in order to locate the enzymatic activities. Two enzymes were clearly resolved, fraction 32 with a PNB/PNC ratio of 4.6 and fraction 51 with a PNB/PNC ratio of 1.40. These have been designated Lipase 1 and Lipase 2, respectively.

The fractions from this column were further analyzed by SDS gel electrophoresis. This analysis revealed that the two enzyme activities track with 30,000 molecular weight bands characteristic of procaryotic enzymes; in addition, Lipase 2 migrated as a doublet, and was clearly resolved from the single and of Lipase 1. Prior to sequence analysis, these two partially purified enzymes were separated from the high and low molecular weight contaminants by reverse phase chromatography.

EXAMPLE 5

Purification of Lipase 1 by HPLC in Preparation for Enzyme Peptide Fragmentation Prior to sequence analysis, the partially purified material of Example 3 was further purified by chromatography on a 4.8×100 mm, SynChromPak C4 reverse phase HPLC column. The system was equilibrated in 0.05% triethylamine (TEA) and 0.05% trifluoroacetic acid (TFA) (Solvent A) at 0.05 mL/min. 100 μg to 1 mg of Lipase 1 was injected onto the column and the protein eluted by a compound gradient of Solvent A and n-propanol containing 0.05% and 0.05% TFA (Solvent B). A typical gradient was +5% from 0 to 20% B and then +0.5% B/minute to 60% B. All enzyme is inactivated by this HPLC solvent system. The protein peaks eluting at about 35% solvent B (Lipase 1) or at about 39% Solvent B (Lipase 2) were collected and used for further sequence analysis and preparation of CNBr fragments.

These experiments are designed to show that enzymes that depolymerize plant surface polymers can increase the effectiveness of herbicides. Several plant species including weeds and crops are used in these experiments.

A number of herbicides from various chemical classes were compared in a multispecies screen for percent chlorosis, necrosis and vigor reduction both with and without application of the enzyme from *Pseudomonas mendocina* ATCC 53552 described earlier. The herbicides were applied to various plants at the manufacturers recommended doses and at 10% and 40% of the recommended dose. Two different enzyme concentrations were used: 0.5 mg/ml (HE) and 0.05 mg/ml (LE) and applied at the rate of 40 gallons/acre. All spraying solutions were at pH 10 and contained 100 mm sodium phosphate each. Ratings were done at 6 and 12 days after the treatment. All the experiments were carried out in a greenhouse.

| Herbicides | 100% recommended dose lbs. active ingredient/acre |
|---|---|
| BASAGRAN herbicide [3-(1-methylethyl)-1H-,2,1,3-benzothiadiazin-4(3H)-one 2,2-dioxide] (E-4) - manufactured by BASF | 1 |
| Atrazine (ATRZ) (L-4) - manufactured by Shell | 2 |
| KARMEX herbicide [3-(3,4-dichlorophenyl)-1,1-dimethylurea] (WO-80) - manufactured by Dupont | 1.6 |
| HYVAR herbicide [5-bromo-6-methyl-3-(1-methylpropyl)-2,4-(1H,3H)-pyrimidinedione] XL (E-2) - manufactured by Dupont | 4 |

Rating

Chlorosis—figures represent percent of plants showing chlorosis.

Necrosis—figures represent percent of plants showing necrosis.

Vigor—figures represent percent of plants showing decreased vigor.

Phytotoxicity—figures represent the average percent of chlorosis, necrosis, and vigor for a given sample.

EXAMPLE 6

Using the conditions and enzymes as described above, the following results were achieved at one and two weeks after administration of HYVAR herbicide [5-bromo-6-methyl-3-(1-methylpropyl)-2,4-( 1H,3H)-pyrimidinedione].

Chlorosis (CHL)

Necrosis (NEC)

Vigor (VIG)

Phytotoxicity (PHY)—the average of the above three readings.

One week after treatment

| | | Barnyard Grass | | | | Soybeans | | | | Giant Fox Tail | | | |
|---|---|---|---|---|---|---|---|---|---|---|---|---|---|
| Enzyme | HYVAR | CHL | NEC | VIG | PHY | CHL | NEC | VIG | PHY | CHL | NEC | VIG | PHY |
| No Enzyme | 10% | 30 | 25 | 30 | 28 | 55 | 75 | 75 | 68 | 40 | 30 | 50 | 40 |
| Low Enzyme | 10% | 50 | 18 | 50 | 39 | 90 | 83 | 90 | 88 | 50 | 30 | 50 | 43 |
| High Enzyme | 10% | 25 | 10 | 50 | 28 | 25 | 50 | 50 | 42 | 18 | 18 | 30 | 22 |
| No Enzyme | 40% | 65 | 30 | 55 | 50 | 45 | 60 | 73 | 39 | 50 | 38 | 55 | 48 |
| Low Enzyme | 40% | 55 | 60 | 63 | 59 | 55 | 88 | 73 | 72 | 43 | 65 | 63 | 57 |
| High Enzyme | 40% | 55 | 50 | 30 | 45 | 45 | 50 | 83 | 59 | 38 | 50 | 63 | 30 |
| No Enzyme | 100% | 50 | 60 | 75 | 62 | 100 | 100 | 100 | 100 | 60 | 60 | 75 | 65 |

| | | Turnip | | | | Alfalfa | | | |
|---|---|---|---|---|---|---|---|---|---|
| Enzyme | HYVAR | CK | NEC | VIG | PHY | CHL | NEC | VIG | PHY |
| No Enzyme | 10% | 70 | 93 | 90 | 84 | 10 | 5 | 10 | 8 |
| Low Enzyme | 10% | 70 | 90 | 93 | 84 | 50 | 5 | 30 | 28 |
| High Enzyme | 10% | 50 | 85 | 83 | 73 | 18 | 0 | 10 | 10 |
| No Enzyme | 40% | 65 | 73 | 85 | 74 | 25 | 5 | 15 | 15 |
| Low Enzyme | 40% | 93 | 95 | 95 | 94 | 30 | 30 | 50 | 37 |
| High Enzyme | 40% | 97 | 97 | 98 | 97 | 30 | 13 | 30 | 24 |
| No Enzyme | 100% | 100 | 95 | 90 | 95 | 50 | 10 | 50 | 37 |

These results show that low enzyme concentrations increases the phytotoxicity of Hyvar on all tested plants. Very high concentrations decrease the phytotoxicity in most cases; suggesting that an optimal concentration of enzyme has to be used for the best effect. Decreased effect at high protein concentration could be a physical effect due to the increase of the viscosity of the solution or blocking the entry of chemicals into leaves.

| | HYVAR [5-bromo-6-methyl-3-(1-methylpropyl)-2,4-(1H,3H)-pyrimidinedione] | Two Weeks after Treatment | | | | | | | | | | | |
|---|---|---|---|---|---|---|---|---|---|---|---|---|---|
| | | Barnyard Grass | | | | Giant Fox Tail | | | | Alfalfa | | | |
| | | CHL | NEC | VIG | PHY | CHL | NEC | VIG | PHY | CHL | NEC | VIG | PHY |
| No Enzyme | 18% | 85 | 78 | 78 | 80 | 65 | 63 | 63 | 64 | 55 | 58 | 58 | 57 |
| Low Enzyme | 18% | 88 | 85 | 85 | 86 | 73 | 73 | 73 | 73 | 100 | 100 | 100 | 100 |
| High Enzyme | 18% | 95 | 88 | 88 | 90 | 75 | 75 | 75 | 75 | 100 | 100 | 100 | 100 |

High HYVAR herbicide [5-bromo-6-methyl-3-(1-methylpropyl)-2,4-( 1H,3H)-pyrimidinedione] was 100% kill for all other tested conditions after two weeks.

Ratings done two weeks after the herbicide also showed that enzyme increased the phytotoxicity of HYVAR herbicide.

EXAMPLE 7

The following results were using the method of Example 1 with herbicides from various chemical families. Ratings were done two weeks after the treatment.

| | | SOYBEANS | | | | TURNIP | | | |
|---|---|---|---|---|---|---|---|---|---|
| ENZYME | ATRAZINE | CHL | NEC | VIG | PHY | CHL | NEC | VIG | PHY |
| No Enzyme | 10% | 10 | 33 | 50 | 34 | 38 | 23 | 50 | 37 |
| Low Enzyme | 10% | 38 | 58 | 48 | 48 | 50 | 38 | 50 | 46 |
| High Enzyme | 10% | 55 | 18 | 13 | 12 | 25 | 25 | 25 | 25 |
| No Enzyme | 40% | 55 | 63 | 55 | 58 | 70 | 70 | 83 | 74 |
| Low Enzyme | 40% | 100 | 100 | 100 | 100 | 90 | 90 | 90 | 90 |
| High Enzyme | 40% | 80 | 88 | 88 | 85 | 75 | 88 | 88 | 84 |
| | | SOYBEANS | | | | TURNIP | | | |
| ENZYME | BASAGRAN | CHL | NEC | VIG | PHY | CHL | NEC | VIG | PHY |
| No Enzyme | 10% | 5 | 5 | 13 | 8 | 25 | 25 | 38 | 29 |
| Low Enzyme | 10% | 18 | 43 | 50 | 37 | 38 | 63 | 75 | 59 |
| High Enzyme | 10% | 18 | 38 | 73 | 43 | 38 | 50 | 63 | 50 |

Plants were completely killed with BASAGRAN herbicide [3-(1-methylethyl)-1H-,2,1,3-benzothiadiazin- 4(3H)-one 2,2-dioxide] applied at 40% of the recommended dosage, KARMEX herbicide [3-(3,4-dichlorophenyl)-1,1-dimethylurea] showed increased phytotoxicity with enzyme when sprayed on turnips.

From these experiments, it is clear that herbicides from four different chemical families showed increased phytotoxicity when applied with a depolymerase enzyme such as cutinase.

EXAMPLE 8

The method of Example 1 was used except that the enzyme was applied 2 hours prior to administering the agricultural chemical with the following results. Ratings were done two weeks after treatment

| | | SOYBEANS | | | | TURNIPS | | | |
|---|---|---|---|---|---|---|---|---|---|
| ENZYME | KARMEX | CHL | NEC | VIG | PHY | CHL | NEC | VIG | PHY |
| No Enzyme | 10% | 0 | 0 | 0 | 0 | 28 | 10 | 0 | 13 |
| Low Enzyme | 10% | 0 | 0 | 0 | 0 | 18 | 15 | 5 | 11 |
| High Enzyme | 10% | 0 | 0 | 0 | 0 | 18 | 15 | 0 | 11 |
| No Enzyme | 40% | 0 | 10 | 0 | 3 | 25 | 38 | 37 | 33 |
| Low Enzyme | 40% | 0 | 15 | 5 | 6 | 30 | 50 | 43 | 41 |
| High Enzyme | 40% | 0 | 13 | 10 | 8 | 35 | 25 | 50 | 36 |

Phytotoxicity of KARMEX herbicide [3-(1-methylethyl)-1H-,2,1,3-benzothiadiazin- 4(3H)-one 2,2-dioxide] under the test conditions were low. At 40% of the recommended

| | BASAGRAN herbicide [3-(1-methylethyl)-1H-2,1,3-benzothiadiazin-4(3H)-one 2,2-dioxide] | Soybeans | | | | Turnip | | | |
|---|---|---|---|---|---|---|---|---|---|
| | | CHL | NEC | VIG | % PHY | CHL | NEC | VIG | % PHY |
| No Enzyme | 10% | 25 | 25 | 25 | 25 | 25 | 63 | 55 | 48 |
| Low Enzyme | 10% | 48 | 48 | 48 | 48 | 63 | 85 | 85 | 78 |
| High Enzyme | 10% | 0 | 5 | 0 | 2 | 30 | 50 | 43 | 41 |

This example illustrates that enzyme can be sprayed prior to the herbicide spray and still obtain increased phytotoxicity with enzyme. When chemicals that are inhibitory to the enzymes are used, this method can be applied to obtain increased phytotoxicity.

UPTAKE OF RADIOLABELED AGRICULTURAL CHEMICALS INTO LEAF DISCS

Experimental Procedure

Leaf discs (1 cm diameter) were prepared from 9–13 day old soybean plants, and planed them on a nitrocellulose paper that was presoaked with 100 ug/ml stocptomycin in a petri dish. Radioactive chemicals were dissolved in 100 mM sodium phosphate buffer containing 0.05% TRITON X-100 surfactant 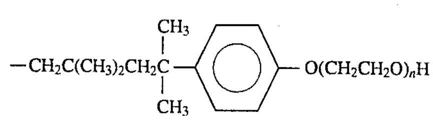 where n is an integer from 9 to 10 In addition to TRITON surfactant, ($^{14}$C) uracil solution contained 0.4% ethanol, ($^{14}$C) atrazine contained 10% ethanol ($^{14}$C) indole acetic acid contained 2% ethanol and ($^{14}$C) urea contained 0.2% ethanol. 5 ul of the radioactive chemical solution (9/uci/ml) was applied on the leaf disc and incubated for 5–7 hr at room temperature. After the incubation, leaf discs were rinsed 3 times with 0.025% TRITON X-100 surfactant solution and transferred into separate scintillation vials. Radioactivity taken up by each leaf disc was determined by a scintillation counter after adding 10 ml of Ecolite scintillation fluid into each vial. Ten leaf discs were used for each data point in all experiments. All radioactive chemicals were obtained from Amersham (U.S.A.). The specific activities of the chemicals were as follows:

indolyl (2-$^{14}$C) acetic acid, 319 uci/mg (ethyl-1-$^{14}$C) atrazine, 116 uci/mg ($^{methyl}$ $^{14}$C) diuron, 243 uci/mg ($^{14}$C) urea, 1 mci/mg (2-$^{14}$C) uracil, 474 uci/mg

Enzymes

Cutinase enzyme same as before.

Macerating enzyme, GC219, is an enzyme mixture sold by Genencor which comprises of cellulase, pectinase and hemicellulase.

Inactive protein control for cutinase was a cutinase mutant with an analine substitution at position 126 for serine. This yields an inactive enzyme. For GC219, an equivalent amount of bovine serum albumin was used as inactive protein control.

UPTAKE OF CHEMICALS INTO PLANT LEAVES

EXAMPLE: Enhancement of Uracil ($^{14}$C) Uptake by Cutinase and Macerating Enzymes (CG219)

| pH | Cutinase ug/ml | GC219 mg/ml | Radioactivity (cpm) Inactive Protein Control | Active Enzyme |
|---|---|---|---|---|
| 7.0 | 200 | — | 816 ± 214 | 4070 ± 1160 |
| 7.0 | 100 | — | 2180 ± 724 | 8075 ± 1162 |
| 7.0 | 50 | — | 1340 ± 696 | 3470 ± 684 |
| 10 | 200 | — | 481 ± 124 | 869 ± 364 |
| 10 | 100 | | 234 ± 37 | 477 ± 230 |
| 7.0 | — | 15.7 | 1941 ± 315 | 5191 ± 1745 |

*At pH 7.0 uptake without any addition of protein was 2090 ± 549 and at pH 10 it was 507 ± 162.

Conclusions

1. Active cutinase and macerating enzymes enhance uptake of uracil.

2. pH 7.0 is better for uracil uptake than pH 10.

PLANT GROWTH REGULATOR

EXAMPLE: Enhancement of Indole Acetic Acid (IAA) Uptake by Cutinase and Macerating Enzymes

| pH | Cutinase ug/ml | GC219 mg/ml | Radioactivity (cpm) Inactive Protein Control | Active Enzyme |
|---|---|---|---|---|
| 7.0 | 100 | — | *1712 ± 339 | 7091 ± 794 |
| 9.0 | 100 | — | 3250 ± 513 | 4157 ± 2050 |
| 7.0 | 50 | — | 1261 ± 408 | 5619 ± 2254 |
| 7.0 | — | 7.9 | **402 ± 197 | 2052 ± 902 |
| 7.0 | 50 | 7.9 | 540 ± 135 | 9116 ± 2383 |

*For lipase inactive protein control was A126.
**For GC219 inactive protein control was BSA.
***Background uptaken of IAA without any addition of protein was 1292 ± 146.

Conclusions

1. IAA uptake is increased by treatment with active cutinase and active macerating enzymes.

2. IAA uptake at pH 7.0 is better than at pH 9.0.

3. Combination of enzymes is better than individual enzymes alone for the uptake of IAA.

HERBICIDE

EXAMPLE Enhancement of Atrazine and Diuron Uptake by Cutinase

| pH | Cutinase ug/ml | Inactive Protein Control* | Radioactivity (cpm) Active Enzyme |
|---|---|---|---|
| Herbicide | | | |
| 7.0 Atrazine | 200 | 31097 ± 2959 | 54133 ± 2874 |
| 7.0 Diuron | 100 | 24832 ± 2834 | 42684 ± 2333 |
| 10 | 200 | 6878 ± 2126 | 8592 ± 803 |

*Inactive protein control was A126.
**Without any addition of protein, atrazine uptake was 24007 ± 3984.
***Without any addition of protein, Diuron uptake was 5739 ± 1376.

Conclusion

Active cutinase increased uptake of herbicides.

FERTILIZER

EXAMPLE: Enhancement of ($^{14}$C) Urea Uptake by Cutinase

| pH | Cutinase ug/ml | Inactive Protein Control* | Radioactivity (cpm) Active Enzyme |
|---|---|---|---|
| 7.0 | 200 | 934 ± 168 | 1167 ± 101 |
| 10 | 200 | 466 ± 36 | 911 ± 139 |
| 10 | 100 | 224 ± 60 | 471 ± 48 |

*Inactive protein control was A126.
**Without any additions as pH 7.0 urea uptake was 785 ± 141 and at pH 10 it was 398 ± 43.

Conclusions

1. Cutinase increases uptake of a urea into leaf discs.
2. Uptake of urea at pH 10 appears to be better than at pH 7.0

EXAMPLE 10

FUNGICIDE UPTAKE IN SOYBEAN PLANTS

Experimental Procedure

The difoliate leaflets of 9–13 day old soybeam plants were treated with solutions of cutinase (100 ug/ml), BENOMYL fungicide [1-(butylcarbamoyl)-2-benzimidazolecarbamic acid methyl ester] (1 mg/ml), and GC219 (12.6 mg/ml) alone and BENOMYL fungicide [1-(butylcarbamoyl)-2-benzimidazolecarbamic acid methyl ester] plus enzymes. The solutions were dissolved in 100 mM sodium phosphate, pH 7 containing 0.5% TRITON surfactant

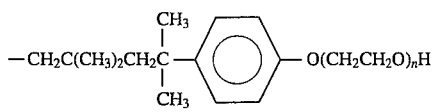

where n is an integer from 9 to 10 X-100. In addition to TRITON X-100 surfactant,

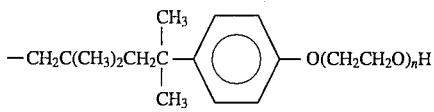

where n is an integer from 9 to 10 the BENOMYL fungicide [1-(butylcarbamoyl)-2-benzimidazolecarbamic acid methyl ester] contained 5% Dimethyl formamide. For each experiment 100 ul of solution was applied in 5 ul droplets to each difoliate leaflet. Duplicate plants were treated in this manner. The treated plants were incubated for two hours under normal greenhouse conditions. Identical solutions as those applied to the plants were also incubated for two hours to assure chemical stability under greenhouse conditions. After the incubation, the treated leaves were cut at the petiole and rinsed with a 0.05% TRITON X-100 surfactant

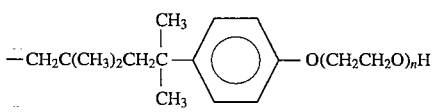

where n is an integer from 9 to 10 solution. Both difoliates were then ground with a mortar and pestle with 1.5 ml of a 100 mM sodium phosphate, pH 7 buffer. The extract was centrifuged and the supernatant was sterile filtered through a 0.45 um disc. The supernatant was then added to CMA media containing 2% agar to yield a final volume of 10 mls. 5 mls was them poured into a single well in a 6 well culture plate. Serial dilutions were made for each solution to achieve 1:1, 1:2 and 1:4 dilution of the plant extract in the agar.

Once the agar was solidified each well was innoculated with spores of *Trichoderma reesei* QM6A strain. The plates were incubated at 30° C. for 24 hours and the growth of *T. reesei* was rated.

Materials

Enzymes
a) Cutinase enzyme same as before.
b) GC219 (macerating enzyme blend) is an enzyme mixture sold by Genencor.

Fungal Strain

*T. reesei* QM6A—Obtained from ATCC (ATCC 13631)

Fungicide

BENOMYL fungicide [1-(butylcarbamoyl)-2-benzimidazolecarbamic acid methyl ester] was purchased from Rod McLellan Company (South San Francisco, Calif.)

Media 0.05 mg/ml streptomycin

CMA Media: 2% Agar 1.0 gm bacto-peptone
20 gm malt extract per 1 liter DI H$_2$O
20 gm glucose

Rating

−no inhibition ++=good inhibition

+weak inhibition +++=strong inhibition

Results of Fungicide uptake into Plant Leaves

| Description | Inhibition of Fungal Growth |
|---|---|
| Control untreated | − |
| Buffer | − |
| BENOMYL fungicide [1-(butylcarbamoyl)-2-benzimidazolecarbamic acid methyl ester] (1:1 dilution) | − |
| BENOMYL fungicide [1-(butylcarbamoyl)-2-benzimidazolecarbamic acid methyl ester] (1:2 dilution) | − |
| BENOMYL fungicide [1-(butylcarbamoyl)-2-benzimidazolecarbamic acid methyl ester] (1:4 dilution) | − |
| Cutinase (1:1 dilution) | − |
| Cutinase (1:2 dilution) | − |
| Cutinase (1:4 dilution) | − |
| Cutinase and BENOMYL fungicide [1-(butylcarbamoyl)-2-benzimidazolecarbamic acid methyl ester] (1:1 dilution) | +++ |
| Cutinase and BENOMYL fungicide [1-(butylcarbamoyl)-2-benzimidazolecarbamic acid methyl ester] (1:2 dilution) | ++ |
| Cutinase and BENOMYL fungicide [1-(butylcarbamoyl)-2-benzimidazolecarbamic acid methyl ester] (1:4 dilution) | + |
| GC219 (1:1 dilution) | − |
| GC219 (1:2 dilution) | − |
| GC219 (1:4 dilution) | − |
| GC219 and BENOMYL fungicide [1-(butylcarbamoyl)-2-benzimidazolecarbamic acid methyl ester] (1:1 dilution) | ++ |
| GC219 and BENOMYL fungicide [1-(butylcarbamoyl)-2-benzimidazolecarbamic acid methyl ester] (1:2 dilution) | + |
| GC219 and BENOMYL fungicide [1-(butylcarbamoyl)-2-benzimidazolecarbamic acid methyl ester] (1:4 dilution) | − |

Conclusion

Cutinase and macerating enzymes increased uptake of BENOMYL fungicide [1-(butylcarbamoyl)-2-benzimidazolecarbamic acid methyl ester] into soybean plants.

EXAMPLE 11

HYVAR UPTAKE BY WHOLE PLANTS: EFFECT OF MACERATING ENZYMES (GC 219)

Experimental Procedure

13–16 day old Beefsteak Tomato seedlings were treated with solutions of HYVAR herbicides [5-bromo-6-methyl-3-(1-methylpropyl)-2,4-(1H,3H)-pyrimidinedione] and GC219. Solutions of Hyvar and GC219 were made up on DI H$_2$O and 1% ethanol and adjusted with 0.1N HCL to a final pH of 4.0. 10 ul of solution was applied to each cotyledon and 15 ul to each secondary pentafoliate leaflet. 10 tomato seedlings were used for each test solutions. Observations were made daily after treatment for 4 days.
Rating −=No phytotoxicity
+=Some phytotoxicity seen in area of treatment.
++=Phytotoxicity seen outside area of treatment.

Materials

Enzyme —GC219 is a mixture of enzymes sold by Genencor.
HYVAR herbicides [5-bromo-6-methyl-3-(1-methylpropyl)-2,4-(1H,3H)-pyrimidinedione] XL—formulated herbicide (DUPONT).
HYVAR herbicide [5-bromo-6-methyl-3-(1-methylpropyl)-2,4-(1H,3H)-pyrimidinedione] was diluted 1:200 or 1:400 for each experiment.

| DATA | PHYTO-TOXICITY RATING | |
|---|---|---|
| | Day 1 | Day 2 |
| 1. No treatment | − | − |
| 2. HYVAR herbicide [5-bromo-6-methyl-3-(1-methylpropyl)-2,4-(1H,3H)-pyrimidinedione] alone (1:200 dilution) | − | + |
| 3. HYVAR herbicide [5-bromo-6-methyl-3-(1-methylpropyl)-2,4-(1H,3H)-pyrimidinedione] + 6.28 mg/ml GC219 | + | ++ |
| | Day 2 | Day 3 |
| 1. Control | − | − |
| 2. HYVAR herbicide [5-bromo-6-methyl-3-(1-methylpropyl)-2,4-(1H,3H)-pyrimidinedione] (1:400 dilution) | − | − |
| 3. HYVAR herbicide [5-bromo-6-methyl-3-(1-methylpropyl)-2,4-(1H,3H)-pyrimidinedione] + 6.28 mg/ml GC219 | + | ++ |
| 4. HYVAR herbicide [5-bromo-6-methyl-3-(1-methylpropyl)-2,4-(1H,3H)-pyrimidinedione] + 12.6 mg/ml GC219 | ++ | ++ |

Conclusion

Macerating enzymes (GC219) enhances uptake of HYVAR herbicide [5-bromo-6-methyl-3-(1-methylpropyl)-2,4-(1H,3H)-pyrimidinedione] into tomato plants.

What is claimed is:

1. A composition comprising a herbicide which is not inhibitory of enzyme action and a cutinase enzyme capable of degrading at least a portion of the plant cell polymer of a plant.

2. A composition according to claim 1 wherein said cutinase is obtained from *Pseudomonas mendocina* ATCC 53552.

3. A kit comprising separately a herbicide which is not inhibitory of enzyme action and a cutinase enzyme capable of degrading at least a portion of the plant cell polymer of a plant.

4. A kit according to claim 3 wherein said cutinase is obtained from *Pseudomonas mendocina* ATCC 53552.

5. A composition comprising a cutinase enzyme which is capable of degrading at least a portion of the plant cell polymer of a plant and atrazine (6-chloro-N-ethyl-N'-(1-methylethyl)-1,3,5-triazine- 2,4-diamine).

6. A composition according to claim 5 wherein the cutinase is obtained from *Pseudomonas mendocina* ATCC 53552.

7. A kit comprising separately a cutinase enzyme which is capable of degrading at least a portion of the plant cell polymer of a plant and atrazine (6-chloro-N-ethyl-N'-(1-methylethyl)- 1,3,5-triazine-2,4-diamine).

8. A kit according to claim 7 wherein the cutinase is obtained from *Pseudomonas mendocina* ATCC 53552.

9. A composition comprising a cutinase enzyme which is capable of degrading at least a portion of the plant cell polymer of a plant and BENOMYL fungicide (1-(butylcarbamoyl)- 2-benzimidazolecarbamic acid methyl ester).

10. A kit comprising separately a cutinase enzyme which is capable of degrading at least a portion of the plant cell polymer of a plant and BENOMYL fungicide (1-(butylcarbamoyl)-2-benzimidazolecarbamic acid methyl ester).

* * * * *